United States Patent [19]

Koprowski et al.

[11] Patent Number: 4,471,057

[45] Date of Patent: Sep. 11, 1984

[54] DETECTION OF COLORECTAL CARCINOMA

[75] Inventors: Hilary Koprowski, Wynnewood; Zenon Steplewski, Strafford; Meenhard Herlyn, Wynnewood, all of Pa.

[73] Assignee: The Wistar Institute, Philadelphia, Pa.

[21] Appl. No.: 246,187

[22] Filed: Jun. 30, 1981

[51] Int. Cl.$^3$ ...................... G01N 33/54; G01N 33/56
[52] U.S. Cl. .................................... 436/518; 436/531; 436/542; 436/548; 436/804; 436/813
[58] Field of Search .......................... 424/1, 1.5, 1.1, 9, 424/85, 177; 23/230 B, 915, 923; 436/548, 536–542, 504, 518, 531, 53, 543–545, 547, 548, 804, 813, 815; 435/4, 7, 68, 70, 172, 240, 241, 948; 260/112 R

[56] References Cited

U.S. PATENT DOCUMENTS 4,172,124 10/1979 Koprowski et al. ..................... 424/1
4,349,528 9/1982 Koprowski et al. ..................... 424/1

OTHER PUBLICATIONS

Herlyn et al., European Journal of Immunology, vol. 9, pp. 657–659, (8–1979).
Herlyn et al., Cancer Research, vol. 40, pp. 717–721, (3–1980).
Herlyn et al., International Journal of Cancer, vol. 27, pp. 769–774, (1981).
Gilliland et al., Proc. National Academy Sciences, USA, vol. 77, No. 8, pp. 4539–4543, (8–1980).
Marx, J. L., Science, vol. 216, pp. 283–285, (4–1982).
Herlyn et al., Proc. National Academy Sciences, USA, vol. 76, No. 3, pp. 1438–1442, (3–1979), "Colorectal Carcinoma".
Koprowski et al., Aromatic Cell Genetics, vol. 5, pp. 957–972, (1979).
Koprowski et al., Science, vol. 212, pp. 53–55, (4–1981), "Specific Antigen . . . ".
Magnani et al., Science, vol. 212, pp. 55–56, (4–1981), "A Monosialoganglioside . . . ".

*Primary Examiner*—Benjamin R. Padgett
*Assistant Examiner*—M. Moskowitz
*Attorney, Agent, or Firm*—Banner, Birch, McKie & Beckett

[57] ABSTRACT

Colorectal carcinoma is detected by testing body fluids for the colorectal carcinoma monosialoganglioside identified by monoclonal antibodies produced by fused cell hybrid ATCC HB 8059.

8 Claims, No Drawings

DETECTION OF COLORECTAL CARCINOMA

The invention described herein was made in the course of work under a grant or award from the Department of Health, Education and Welfare.

DESCRIPTION OF THE INVENTION

Most of the tests developed for immunodiagnosis of digestive system tumors by detection of circulating tumor-associated antigens such as carcinoembryonic antigen (CEA), alpha-fetoprotein and others lack the specificity to make a confident distinction between cancer and control groups of patients. Particularly disturbing is the fact that many healthy persons or patients with a non-malignant disease circulate within their bodies of one or another of the antigens purported to be of specific diagnostic value for cancer patients. For example, extensive exploration of carcinoembryonic antigen (CEA) as a diagnostic tool for colorectal cancer (CRC) revealed that, although most CRC patients have CEA in their sera, many sera obtained from patients with ulcerative colitis, alcoholic cirrhosis, pulmonary emphysema and other primary site carcinomas, also bind anti-CEA antibody in radioimmune assays (RIA). Furthermore, about one fifth of all healthy subjects who smoke cigarettes also have CEA in their sera.

There is an obvious need for an assay that will identify, with a good degree of reliability, those individuals who have colorectal carinoma and which will not provide a spectrum of disturbing and expensive false positives when healthy patients are tested.

It is one object of this invention to provide a test that has substantial specificity for colorectal carcinoma.

It is another object of this invention to provide a hybrid cell which produces an antibody that has substantial specificity for colorectal carcinoma.

According to this invention there is provided a method for the detection of colorectal carcinoma which comprises testing body fluid for the presence of the colorectal carcinoma monosialoganglioside identified by the antibody produced by the fused cell hybrid ATCC No. HB 8059.

In one specific aspect of this invention there is provided an assay for the detection of colorectal carcinoma which comprises testing body fluid for the presence of the colorectal carcinoma monosialoganglioside identified by the antibody produced by the fused cell hybrid ATCC No. HB 8059, hereafter referred to as KS monosialoganglioside by the procedure comprising:

(a) incubating an aliquot of anti-KS monosialoganglioside monoclonal antibodies produced by a fused cell hybrid with an aliquot of cell free body fluid from an individual;

(b) incubating the mixture from (a) above in contact with a surface having said colorectal carcinoma monosialogangliosides attached thereto;

(c) washing said mixture from said surface after said incubation of (b);

(d) measuring the amount of antibody bound to said surface; and (e) comparing the results obtained with results obtained when steps (a) to (d) are performed but a buffer solution is employed in step (a) to replace the body fluid.

This invention permits the detection of colorectal carcinoma not only in clinically diagnosed CRC patients but also in patients in an early stage of disease, when prompt surgical intervention may be warranted.

In accordance with this invention, it has been discovered that an extra-cellular antigen is present in the body fluid of CRC patients that cannot be detected in healthy subjects, in patients suffering from chronic inflammatory disease of the bowel or in patients suffering from other cancers. The only exception to this was detection of the antigen in two cases of pancreatic carcinoma and two cases of gastric carcinoma, carcinomas which have the same endodermal origin as CRC cells. Presence of the antigen in this case may be advantageous, given the usual difficulty in diagnosing this type of cancer during its early growth stages.

The monoclonal antibodies contemplated for use in this invention bind specifically to an antigen of CRC cells and not to an antigen of cells of other cancers, with the exception of carcinomas of the stomach and of the pancreas maintained in culture, which tumors have the same endodermal origin as CRC cells. The nature of the antigen recognized by the monoclonal antibody may account for the high specificity of reaction. It is not CEA, since binding of anti-CRC antibody to CRC cells was not inhibited by purified CEA obtained from the diagnostic kit of either Hoffman La Roche or Abbot Diagnostics. Moreover, no correlation was observed between the presence of CEA in the blood of patients and healthy volunteers and the results of the inhibition assay of this invention. Relation of the antigen detected by the anti-CRC antibody to other tumor-associated antigens such as $B_2$-microglobulin can be ruled out, since the antigen recognized by anti-CRC antibody is not a protein: the antigen is stable under conditions such as incubation at 37° C. for two weeks, drying and heating to 85° C. Studies have indicated that the antigen is a monosialoganglioside not found in normal adult tissues.

The KS-monosialoganglioside antigen is present in the lipid extract of CRC cells and is identified by the antibody produced by fused cell hybrid ATCC No. HB 8059, deposited with the American Type Culture Collection (ATCC), 12301Parklawn Drive, Rockville, Md. 20852. A variety of known testing procedures can be employed to test for its presence in body fluids, such as blood, cell free serum or urine. Such procedures include without limitation, radioimmunoassay with radio labled monoclonal antibodies, an agglutination inhibition assay, an enzyme linked assay, chemical analysis, and the like. Such assays can be carried out with the fluids containing such cells as may be present but preferably are carried out with cell-free fluids. The inhibition assay employing monoclonal antibodies is a preferred assay for the practice of this invention.

Antibodies useful in this invention can be obtained by challenging an animal with a monosialoganglioside-containing CRC cell fraction from a patient with colorectal carcinoma, forming a fused cell hybrid between antibody producting cells from said animal and myeloma cells, cloning said hybrids and selecting clones which produce antibodies that bind with said KS monosialoganglioside. Techniques for challenging animals, preparing fused cell hybrids and testing for the binding capacity of antibodies are known to the art and are described, inter alia, in U.S. Pat. No. 4,172,124, *Somatic Cell Genetics*, Vol. 5, No. 6, pp 957–972 (1979), and Kennett, *Monoclonal Antibodies*, Plenum Press (1980). The particular species of animal from which the myeloma and antibody producing cells are selected are not critical insofar as it is possible to use cells of the same species or to fuse cells of one species with another, for example, mouse to mouse, rat to rat or mouse to rat.

Antibodies which interfere with the binding of antibodies produced by hybrid cell line ATCC No. HB 8059 are preferred for the assay of this invention. Antibodies corresponding to those produced by hybrid cell line ATTC No. HB 8059 are particularly preferred for the assay of this invention.

The inhibition assay can employ an aliquot of a cell free body fluid including serum or urine. Blood serum obtained by removing the cells from blood is preferred and, for ease of presentation, the following description will be in terms of serum. It is to be understood, however, that other body fluids are expressly contemplated for use in this assay.

According to the assay, an aliquot of serum is incubated with an aliquot of anti-KS monosialoganglioside antibody (i.e., the antibody is permitted to bind to appropriate sites in the serum if such sites are present). After the initial incubation period, the mixture is brought into contact with a surface having attached thereto a monosialoganglioside antigen from a known human CRC cell and again allowed to incubate. For many of the tests herein reported, the human CRC cell line used was SW 1116 obtained from Scott and White Clinic, Temple, Tex. and described, inter alia, in *Somatic Cell Genetics*, Vol 5, No 6, 1979 pp 957–972. The choice of a particular CRC cell line with its attendant KS monosialoganglioside is not critical and many such cells are readily available to the art.

After the second incubation, the mixture is separated from the surface (e.g., by washing) and the amount of antibody bound to the surface is measured. Such measurement can be accomplished using techniques known to the art including, for example, an enzyme linked assay, immuno fluorescences, and radioimmunoassay. Typical techniques are described, inter alia, in Kennett, *Monoclonal Antibodies*, Plenum Press, 1980.

For a radioimmunoassay, the radioactive labeled immunoglobulin should be for the animal species from which the antibody-producing cell of the fused cell hybrid was obtained. The assays described herein employed mouse-mouse fused cell hybrids and [$^{125}$I] rabbit anti-mouse immunoglobulin. In such assay, the surface, following removal of the serum-antibody mixture, was incubated with the radio-labeled anti-mouse immunoglobulin so that it could bind to any monoclonal antibodies that had bound to the surface in the previous incubation.

The precoating of surfaces to provide a surface having an antigen attached thereto is a technique that is known in the art. Such techniques, for example, may use commercially available polyvinyl plates or beads. Indeed, if desired, CRC cells which contain the antigen on their surface can be employed. The primary requisite is a solid to which the monoclonal antibody can bind and thereafter be separated from the liquid mixture.

Maximum binding of antibodies may be determined by incubation of the antibodies with an aliquot of buffer solution instead of the serum. Appropriate buffer solutions for such use are well known in the art and include, inter alia, a phosphate buffered saline solution containing 1% gamma globulin-free horse serum. The antibody-buffer mixture is then incubated with the antigen containing surface and the amount of antibodies which bind to the surface are measured as discussed above.

Background controls may be determined by the incubation of test samples containing serum with aliquots of nonspecific immunoglobulin for the animal species from which the antibody-producing cell of the fused cell hybrid was obtained. While use of background controls is described below and provides best accuracy, the use of such controls is not essential to an effective assay. Direct comparison of test assays with maximum binding assays can also be employed. If background controls are employed the percent inhibition may be calculated according to the formula described below.

The inhibition assay utilizes the competitive binding of an antigen. If the patient's serum contains the antigen from a colon cancer, it will react with the monoclonal antibody forming a bound antibody antigen complex. This complex is no longer able to react in another binding reaction since it has already been bound. If there is no carcinoma antigen in the patients's serum, the monoclonal antibody is not bound and is still reactive.

The mixture is then transferred into contact with a surface having attached KS monosialoganglioside antigen to (e.g., a second small culture well in which has been placed a preparation of human colon cancer cell extract). These have a known amount of the antigen. If in the myriad of material transferred to this well there is free or unbound antibodies this will react with the cell antigen. The amount of antibody can be detected by binding a radioactive isotope to the mouse antibody and the amount of antibody present bound to cells is detected by the amount of isotopes present. In this test the more bound isotope that is present in the second well, the less colon tumor antigen that was present in the first culture, on the other hand, if there is little bound isotope in the second well, the rest was present in the patient's serum. If there was none present in the patient's serum, then he is judged not to have carcinoma, but more importantly if there is material detected in his serum this test has confirmed that he does have colon carcinoma.

In order to illustrate the inhibition assay of this invention more fully, the following is presented as a represntative procedure employing antibodies produced by a mouse-to-mouse fused cell hybrid which utilized P3×63 Ag8 mouse myeloma cells.

Hybridomas secreting anti-CRC antibody into the medium were grown according to the method described in *Somatic Cell Genetics*, Vol 5, No 6, pp 957–972 (1979). The hybridoma medium contained approximately 10 μg antibody per ml. Indirect radioimmunoassay (RIA) for antibody binding to its target is also described in the *Somatic Cell Genetics* article above. Dilutions of hybridoma antibodies were used that exhibited 40 to 50 percent maximal reactivity against a given concentration of target antigen prepared either as membrane extracts or as serum-free tissue culture media (SFTCM) of cell line SW 1116. Diluted antibody to be tested for inhibition was mixed in gelatin-coated polyvinylchloride plates (Cooke Eng. Co., Alexandria, Va.) with equal volume of dilutions of human sera. The mixtures were incubated overnight in a humidified chamber at 4° C. and then transferred to wells of plates precoated with either membrane extracts or serum-free supernatant of SW 1116 cells. After overnight incubation, the plates were washed with cold Vernoal-buffered NaCl solution and then again incubated overnight at 4° C., this time with [$^{125}$I] rabbit IgG anti-mouse F(ab)$_2$. The plates were then washed and the wells separated and counted in a Packard gamma counter.

The percentage of specific inhibition of binding of hybridoma antibodies was calculated from the mean of triplicate wells according to the formula:

percent inhibition =

$$100 - \left[ \frac{\text{test cpm} - \text{control cpm}}{\text{maximum cpm} - \text{control cpm}} \right] \times 100$$

Maximum binding was determined through the incubation of hybridoma antibodies with buffer solution instead of serum samples, and background controls were determined through the incubation of test samples with nonspecific mouse immunglobulin (supernatant from myeloma P3×63 Ag8). Statistically significant differences in inhibitions of binding between the test and control samples can be calculated for each test by the Student's t-test.

The following examples are included for illustrative purposes only and are not intended to limit the scope of the invention.

EXAMPLE 1

BALB/c mice were challenged with a monosialoganglioside of colorectal carcinoma cells (by injection with immunizing colorectal carcinoma cells) and a fused hybrid was obtained from the mouse spleen cells and mouse myeloma cell line P3×63 Ag8. The above procedures were carried out as described in *Somatic Cell Genetics*, Vol 5, No 6, pp 957-972 (1979). Antibody producing fused cell hybrid, ATCC HB 8059 (Wistar No. SW-1116-19-9) was selected and its antibodies were employed in the assays herein.

EXAMPLE 2

Sera were obtained from 33 patients who had advanced adenocarcinoma of the colon and rectum with documented metastases in their liver or lungs, 6 patients with other bowel diseases, including two with multiple polyps and 38 patients with forms of cancer other than colorectal carcinoma, all hospitalized at the Onocologic Hospital, Fox Chase Medical Center, Philadelphia, Pa. The sera were aliquoted, coded and frozen at $-70°$ C. Preoperative patients and those with suspected but unproven recurrent cancer were not included in this study group. An additional 13 sera obtained from CRC patients were provided by Met Path Inc., Bala Cynwyd, Pa. Sera were also obtained from 39 healthy volunteers: 15 females 20 to 40 years of age, ten females 41 to 65 years of age; nine males 20 to 40 years of age and five males 41 to 65 years of age. Fifteen of these 39 healthy subjects were smokers.

Cells of CRC SW-1116 were used as a source of target antigen in the binding assay. This tumor is maintained in tissue culture and secretes its antigen in the tissue culture medium. Either extracts (3M KCl) of the cell membranes or cell-free tissue culture medium (SFTCM) were used.

Assays were conducted as described above. In this assay, a 1:500 dilution of anti-CRC monoclonal antibody was mixed with a dilution of either 1:3 or 1:9 of patients' sera and, after incubation, transferred to wells of plates precoated with 3M KCl membrane extract of SW 1116 tumor cells containing 7 μg protein per well. Inhibition of binding was then determined by RIA. The results are shown in Table 1.

TABLE 1

| % Inhibition by Human Sera of Binding of Antibody | NUMBER OF PATIENTS CLINICALLY DIAGNOSED AS: | | | |
|---|---|---|---|---|
| | Advanced Colorectal Carcinoma | Other Bowel Diseases | Other Malignancies | Healthy Volunteers |
| <10% | 3 (10) | 5 (98) | 34 (90) | 39 (100) |
| 10-19% | 6 (18) | 1 (2) | 2 (5) | 0 |
| over 19% | 24 (72) | 0 | 2 (5) | 0 |
| TOTALS: | 33 | 6 | 38 | 39 |

( ) = refers to percentage of total number of patients.

Of 33 sera from patients with advanced CRC, 24 (72 percent) inhibited binding of anti-CRC hybridoma antibody more than 19 percent ($p<0.025$). Six sera inhibited 10 to 19 percent, and three sera inhibited binding by less than 10 percent. In an additional study of the three patients whose sera inhibited less than 10 percent of the binding reaction, ascitic fluid obtained from one of the patients inhibited binding by 30 percent. This and another patient in the 0 to 10 percent inhibition group showed greater than 20 percent inhibition in serum samples collected at different times.

The above results compared strikingly with the lack of inhibition obtained with 39 sera from health volunteers of different ages, some of whom were heavy smokers; sera of this group inhibited binding an average of 2.6 percent. Of 38 sera obtained from patients with malignancies including 6 breast carcinomas and 17 melanomas, none inhibited binding significantly. The only exceptions to this finding were sera obtained from two patients with carcinoma of the pancreas, which sera inhibited binding by 35 percent and 60 percent and from 2 patients with gastric carcinomas (10-19% range). Sera obtained from three patients with inflammatory bowel diseases (one with colitis, one with proctitis and one with diverticulitis), or from two patients with multiple colonic polyps did not inhibit binding. Serum from one patent, diagnosed as having colitis, inhibited binding in the 10-19% range. It is too soon to exclude the presence of a malignancy in that patient. Each serum listed in Table 1 was tested as a coded sample at least three times in the inhibition assay with reproducible results.

Serum was used freshly draw or frozen and thawed once; sera that have been frozen and thawed several times give erratic results.

EXAMPLE 3

The assay of Example 2 was repeated except that (CRC) SW 1116 SFTCM or cell membrane extract from SW 1116 tumor cells was employed instead of sera. As a control, the same material obtained from WM 47 human melanoma was used to inhibit the binding reaction. The CRC cell membrane extract at concentrations of 5 to 20 g protein per well and SFTCM at concentrations of 10 to 20 μg protein per well inhibited binding of the anti-CRC monoclonal antibody to the target antigen preparation. No inhibition was observed with melanoma SFTCM or melanoma cell membrane extract.

EXAMPLE 4

The following tests were conducted in order to identify the nature of the antigen.

Total lipid extracts of colorectal carcinoma and melanoma cells, and of meconium were obtained according to a method devised for the quantitative extraction of gangliosides from brain tissue and described in *Biochem*

*Biophys Acta*, 617:97–109. One gram wet weight of tissue culture cells or meconium was homogenized in 3 ml H₂O c. 4° C. with a Potter-Elevhjem homogenizer. The homogenate, followed by 5.4 ml chloroform, was added to 10.8 ml methanol with constant stirring. After stirring at room temperature for 30 minutes, the extract was centrifuged at 15,000×g for 10 minutes. The pellet was rehomogenized in 2 ml H₂O and extracted as above with 8 ml chloroform-methanol (1:2). The supernatant solutions from both extractions were combined and evaporated under a stream of dry nitrogen, and the residue was either dissolved in chloroform-methanol (2:1) for application to thin layer chromatography sheets or dissolved in methanol for DEAE-Sephadex chromatography as described in Ledun, *Research Methods in Neurochemistry*, Plenum Pub. Co., 1978, 371–410.

The antigen was detected on thin layer chromatograms by autoradiography with the following modification of a method developed for the detection of gangliosides that bind to cholera toxin: thin layer chromatography sheets (chromagram 100 m thick, 10×10 cm, Eastman Kodak Co., Rochester, N.Y.) were scribed to create twenty 0.5 cm×10 cm lanes. Samples of 1 µl of total lipid extract suitably diluted were spotted on the lanes 1.5 cm from the bottom. The sheet, clamped in a sandwich chamber, was developed in a chromatography tank containing chloroform-methanol-0.25 percent KCl (60:35:8), air-dried, and then soaked for 10 minutes at 4° C. in 0.01M sodium phosphate buffer, pH 7.2, containing 0.15M NaCl, 1 percent polyvinylpyrrolidone ($M_r$ 40,000 pharmaceutical grade; Sigma Chemical Co., St. Louis, Mo.), and 0.1 percent sodium azide (Buffer A). The wet chromatogram was laid horizontally on a slightly smaller, parafilm-covered, glass plate. Serum-free hybridoma culture medium containing about 10 µg antibody per ml[1] was diluted 1:4 with Buffer A and gently pipetted onto the chromatogram (about 50 µl/cm² of chromatogram). After incubation in a humid atmosphere for 6 hours at 4° C., the chromatogram was washed by dipping in six successive changes of 0.01M sodium phosphate buffer, pH 7.2, containing 0.15M NaCl (Buffer B). The chromatogram was then laid horizontally as before and immediately layered with [$^{125}$I] rabbit IgG antimouse F(ab)₂ in Buffer A (10⁶ cpm/ml; about 50 µl/cm² of chromatogram). After incubation in a humid atmosphere for 12 hours at 4° C., the chromatogram was washed six times in Buffer B, air-dried and exposed to XR-2 X-ray film (Eastman Kodak, Col, Rochester, N.Y.) for 50 hours.

Colorectal carcinoma cells were treated with ficin (Sigma Chemical Co., St. Louis, Mo., 2×crystallized) and with *Vibrio cholerae* neuraminidase (Calbiochem, La Jolla, Ca.) as described in *Proc. Natl. Acad. Sci.* USA, 1977, 74:4591–4594.

The binding of the hybridoma antibody to colorectal carcinoma cell line SW 1116 was unaffected by pretreatment of the cells with ficin but abolished by pretreatment of the cells with neuraminidase. This behavior is consistant with the antigen being a ganglioside. Total lipid extracts of cells, which contain gangliosides, were chromatographed and tested for antigen by autoradiography. Antigen was detected in extracts of colorectal carcinoma cells but not in extracts of human melanoma cells, which do not bind antibody. The antigen migrates between the standard gangliosides $G_{M1}$ and $G_{D1a}$ under the conditions employed.

Upon DEAE-Sephadex chromatography of the total lipid extract, the antigen was bound to the DEAS-Sephadex and was eluted from the resin in the monosialoganglioside fraction 0.04M Ammonium acetate in methanol. No antigen was detected either in the disialoganglioside fraction eluted by 0.12M ammonium acetate in methanol or in the tri- and tetrasialoganglioside fraction eluted by 0.5M ammonium acetate in methanol. This property and the antigen's chromatographic mobility is indicative of a large monosialoganglioside.

The antigen was not detected by the autoradiographic method in ganglioside mixtures from human tissues other than colorectal carcinoma. However, the antigen was present in human meconium, which is a rich source of fetal glycolipids.

Since modifications will be apparent to those skilled in the art, it is intended that this invention be limited only by the scope of the appended claims.

We claim:
1. A method for the detection of colorectal carcinoma which comprises providing body fluid from an individual and testing said body fluid for the presence of the colorectal carcinoma monosialoganglioside identified by the antibody produced by the fused cell hybrid ATCC HB 8059.

2. The method of claim 1 wherein the body fluid is serum.

3. An assay for the detection of colorectal carcinoma which comprises testing body fluid for the presence of the colorectal carcinoma monosialoganglioside identified by the antibody produced by the fused cell hybrid ATCC HB 8059, hereafter referred to as KS monosialoganglioside, by the procedure comprising:
   (a) incubating an aliquote of anti-KS monosialoganglioside monoclonal antibodies produced by a fused cell hybrid with an aliquot of cell free body fluid from an individual;
   (b) incubating the mixture from (a) above in contact with a surface having said KS monosialoganglioside attached thereto;
   (c) washing said mixture from said surface after said incubation of (b);
   (d) measuring the amount of antibody bound to said surface; and
   (e) comparing the results obtained with results obtained when steps (a) to (d) are performed but a buffer solution is employed in step (a) to replace the body fluid.

4. The assay of claim 3 wherein the body fluid is serum.

5. The assay of claim 3 or 4 wherein a radioimmunoassay is employed to measure the antibody bound to said surface.

6. The assay of claim 3 or 4 wherein assay steps (a) through (d) are also performed employing a nonspecific innunoglobulin for the species of animal from which the antibody-producing cell of the fused cell hybrid was obtained instead of the serum in step (a).

7. The assay of claim 3 or 4 wherein the antibody is produced by fused cell hybrid ATCC HB 8059.

8. The assay of claims 3 or 4 wherein the antibody employed interferes with the binding of the antibody produced by fused cell hybrid ATCC HB 8059.

* * * * *